United States Patent
Foroni et al.

(10) Patent No.: US 12,127,944 B2
(45) Date of Patent: Oct. 29, 2024

(54) MOULD FOR FORMING AN ORTHOPAEDIC COTYLE SPACER

(71) Applicant: G21 S.R.L., SAN POSSIDONIO (IT)

(72) Inventors: Filippo Foroni, Mirandola (IT); Maurizio Foroni, Mirandola (IT)

(73) Assignee: G21 S.R.L., San Possidonio (IT)

( * ) Notice: Subject to any disclaimer, the term of this patent is extended or adjusted under 35 U.S.C. 154(b) by 559 days.

(21) Appl. No.: 17/234,099

(22) Filed: Apr. 19, 2021

(65) Prior Publication Data

US 2022/0192835 A1    Jun. 23, 2022

(30) Foreign Application Priority Data

Dec. 23, 2020 (IT) .................. 102020000032114

(51) Int. Cl.
*A61F 2/30* (2006.01)
*A61F 2/34* (2006.01)

(52) U.S. Cl.
CPC .......... *A61F 2/30942* (2013.01); *A61F 2/34* (2013.01); *A61F 2002/30672* (2013.01); *A61F 2002/30957* (2013.01); *A61F 2310/00353* (2013.01)

(58) Field of Classification Search
CPC ...... A61F 2/3094; A61F 2/30942; A61F 2/34; A61F 2002/30672; A61F 2002/30957; A61F 2310/00353; A44B 11/2519
See application file for complete search history.

(56) References Cited

U.S. PATENT DOCUMENTS

| | | |
|---|---|---|
| 5,824,078 A | 10/1998 | Nelson et al. |
| 5,981,828 A | 11/1999 | Nelson et al. |
| 6,293,971 B1 | 9/2001 | Nelson et al. |
| 2002/0025358 A1* | 2/2002 | Nelson ............... B29C 43/50 425/422 |
| 2004/0134046 A1* | 7/2004 | Giampavolo ...... A44B 11/2519 24/615 |
| 2009/0157189 A1* | 6/2009 | Hartman ............... B28B 1/24 606/92 |
| 2009/0175978 A1* | 7/2009 | Hawkins ............... A61F 2/36 425/470 |
| 2009/0254193 A1* | 10/2009 | Kerboul ............... B22C 7/02 164/35 |
| 2015/0343684 A1 | 12/2015 | Smith et al. |
| 2018/0133611 A1* | 5/2018 | Cooper ............... A63H 33/001 |
| 2018/0290354 A1 | 10/2018 | Smith et al. |
| 2020/0100900 A1 | 4/2020 | Ferroni et al. |
| 2020/0383789 A1 | 12/2020 | Magagnoli et al. |

FOREIGN PATENT DOCUMENTS

| | | |
|---|---|---|
| EP | 1166724 A1 | 1/2002 |
| EP | 3632381 A1 | 4/2020 |
| WO | 2012158618 A1 | 11/2012 |
| WO | 2017098316 A1 | 6/2017 |

* cited by examiner

*Primary Examiner* — Emmanuel S Luk
*Assistant Examiner* — Victoria Bartlett
(74) *Attorney, Agent, or Firm* — Pearne & Gordon LLP; J. Gregory Chrisman

(57) ABSTRACT

A mould (1) for forming spacers made of medical bone cement is described, comprising a female half-shell (11), provided with a hemispheroidal concavity (13) and a male half-shell (12), provided with a hemispheroidal convexity (14) and insertable in the concavity (13), to define with it an internal space for forming the spacer which has an acetabular shape.

12 Claims, 3 Drawing Sheets

MOULD FOR FORMING AN ORTHOPAEDIC COTYLE SPACER

This invention relates to a mould for forming an orthopaedic cotyle spacer. Orthopaedic spacers made of medical bone cement are well-know to temporarily replace fixed prostheses for the treatment of septic infections or the like. Medical cement prostheses temporarily occupy the space which normally accommodates the fixed prosthesis, preventing, during treatment of the infection, the morphology of the joint from changing and thus preventing re-implantation of the same fixed prosthesis already used by the patient.

Currently, the scope of application of this technology does not cover all the areas of the human skeletal apparatus and in particular does not cover all the joints of the body or parts thereof.

For example, there has long been a need in the market for a temporary prosthesis of the cotyle which can be prepared directly in an operating room by the surgeon, according to the specific morphological requirements of the patient. In detail, there are currently no temporary cotyle prostheses at all, which causes the drawbacks briefly described in the following.

The cotyle or acetabulum is a cup-shaped bone recess located on the outer face of the iliac bone. In the cotyle the head of the femur is inserted and rotates, resulting in the hip joint.

It is well known, those who have undergone an operation to replace the head of femur and the cotyle, for example following removal of a tumour, may be subject to infections affecting the hip in the area around the acetabulum. In practice, the patient has been implanted with a fixed prosthetic joint, for example made of titanium, comprising a cotyle prosthesis fixed to the hip and a prosthesis of the head of the femur.

Currently, for the purpose of infection's treatment, the cotyle prosthesis is removed, with the consequence that the prosthetic head of the femur insists directly on the hip, causing significant pain in patients while walking and not facilitating healing of the infection.

The technical purpose forming the basis of this invention is to propose a mould for making temporary prostheses of the acetabulum which overcome the drawbacks of the prior art, thus satisfying the above-mentioned requirement.

This specified technical purpose is achieved by the invention made according to the appended claims.

Figure 1:
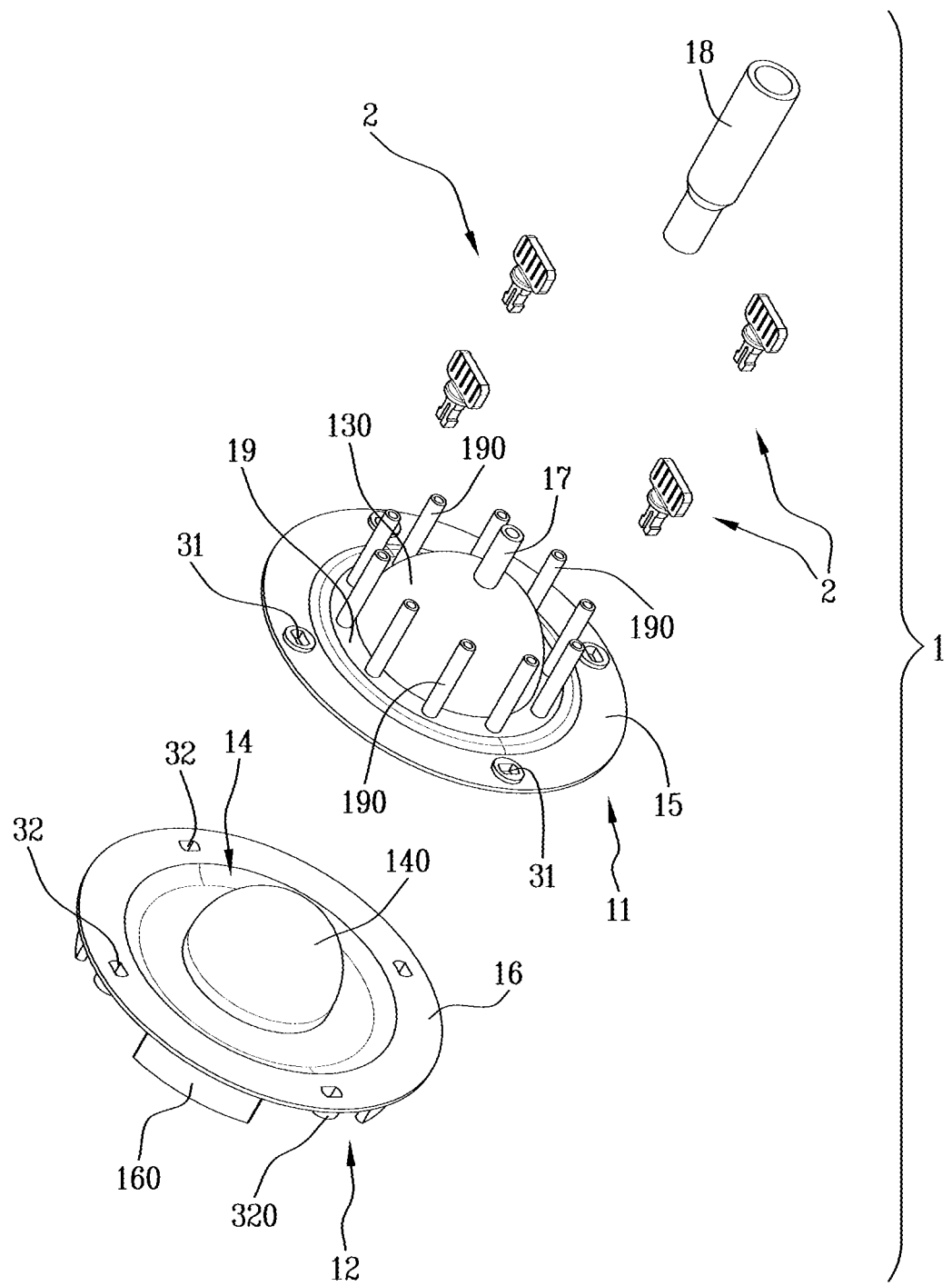
Figure 2:
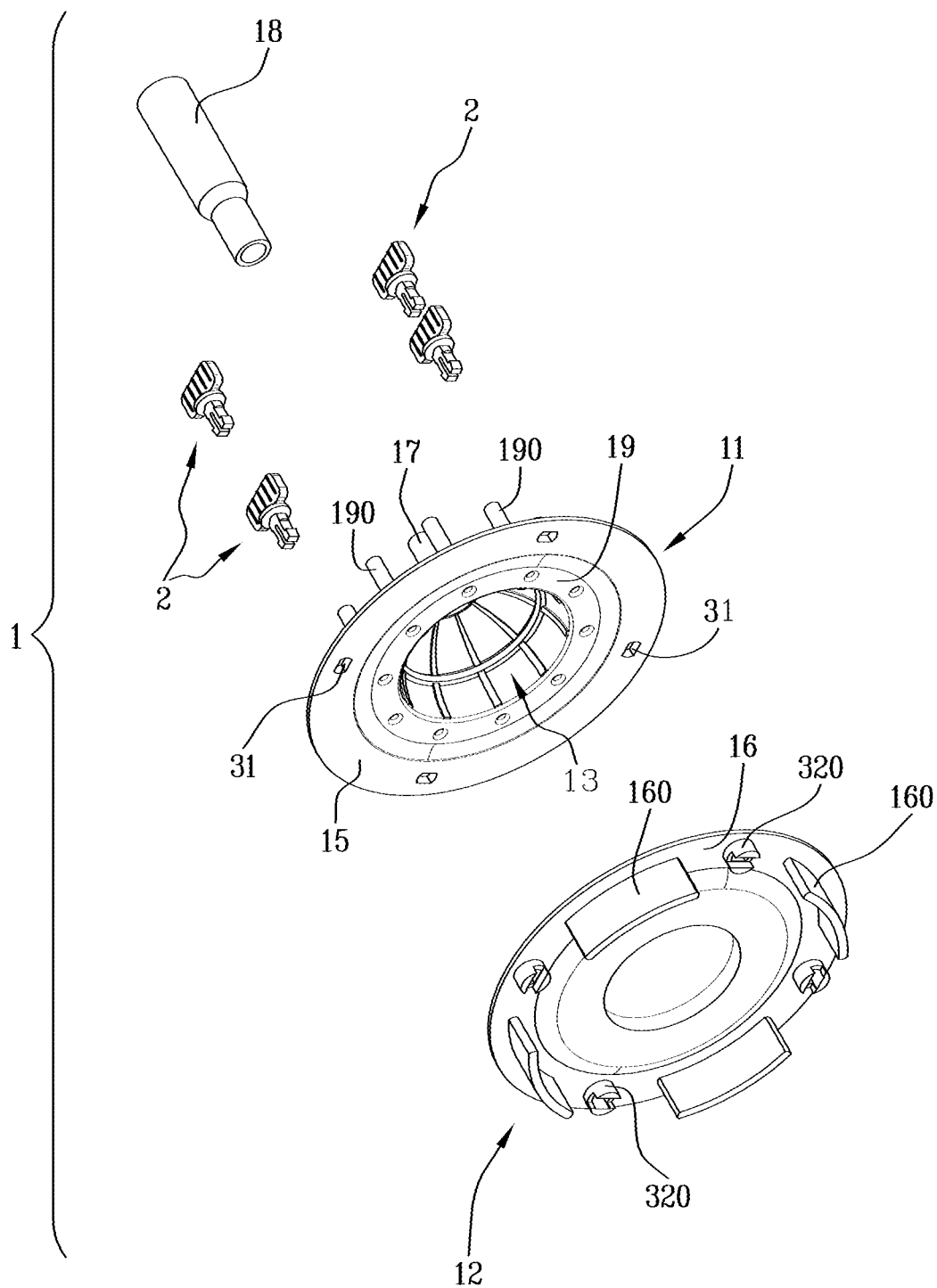
Figure 3:
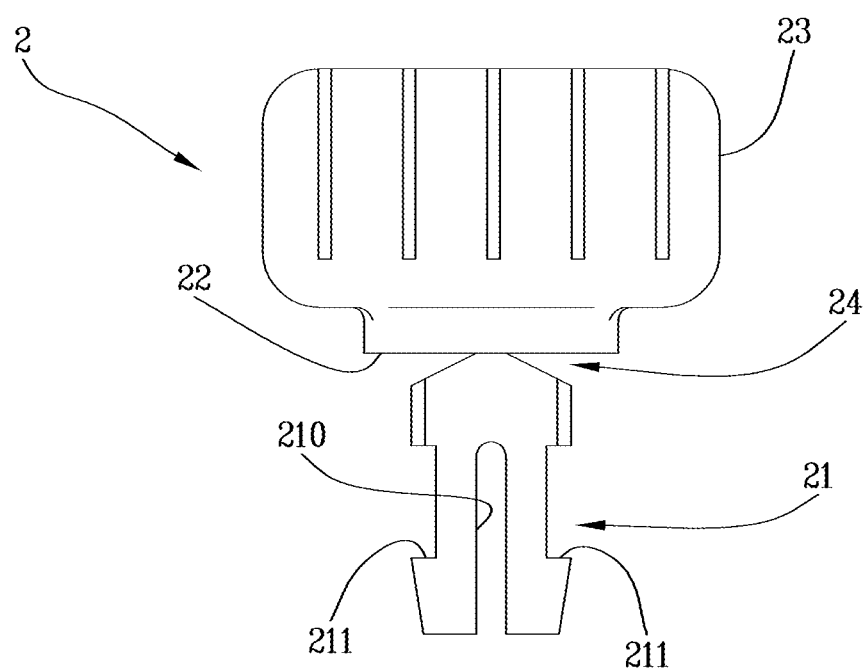

Further features and advantages of the present invention will become more apparent from the non-limiting description of a preferred but not exclusive embodiment of the proposed mould, as illustrated in the appended drawings, in which:

FIGS. 1 and 2 are exploded axonometric views of a mould according to the invention, seen from opposite points of view; and FIG. 3 is an enlarged side view of a locking key included in the mould and illustrated in the previous drawings.

With reference to the appended drawings, the numeral 1 refers collectively to a mould for forming spacers made of medical bone cement, made according to the invention.

As shown in FIGS. 1 and 2, the proposed mould 1 comprises a shell 11, 12, preferably made of plastic material, which includes a female half-shell 11, provided with a hemispheroidal concavity 13 and a male half-shell 12, provided with a hemispheroidal convexity 14.

The term "spheroid" is used here to mean a shape similar to a sphere or an ellipsoid; therefore, the shape of the concavity 13 and the convexity 14 may also be, in a particular case, precisely hemispherical but it can also be more flattened or elongate than an equatorial circumference.

According to an important aspect of the invention, the two half-shells 11, 12 can be brought into contact in such a way that the convexity 14 of the male half-shell 12 enters the concavity 13 of the other half-shell 11, to define between them a hollow space comprising an internal space for the spacer. The internal forming space has an acetabular shape, that is to say, it substantially has the shape of a bowl and is suitable for making a prosthesis made of medical cement, that is, for a so-called "spacer", designed for temporarily replacing the fixed cotyle prosthesis, for the purpose of the treatment of the infection described in the introduction.

Both the half-shells 11, 12 may include a respective cap 130, 140 and, in that case, the convexity 14 of the male half-shell 12 and the concavity 13 of the female half-shell 11 may be defined respectively by the outer and inner surface of the respective cap 130, 140, the cap of the male smaller in size than that of the female. Therefore, the forming space is formed between the outer surface of the cap 140 of the male half-shell 12 and the inner surface of the cap 130 of the other half-shell 11.

As shown in the appended drawings, in the preferred embodiment of the invention, each half-shell 11, 12 comprises a flange 15, 16 extending radially from the perimeter of the base of the respective cap 130, 140; the flange 15, 16 may have an annular shape.

In other words, both the half-shells 11, 12 comprise respective flanges 15, 16 which form, centrally, in one case the cap 130 which forms the above-mentioned concavity 13 and in the other case the cap 140 which forms the convexity 14.

The flange 16 of the male half-shell 12 is designed to abut with that of the female half-shell 11, so as to close the mould 1, when the convexity 14 of the former fits into the concavity 13 of the latter, thereby defining the above-mentioned forming space.

In practice, the upper side of the flange 16 of the male half-shell 12, facing the side of the convexity 14 thereof, is designed to abut with the lower side of the flange 15 of the female half-shell 11, facing the opposite side respect to the concavity 13 (that is, at the cap 130 thereof), thereby defining an end stop for inserting the convexity 14, and thereby automatically defining the space for forming the temporary prosthesis.

The female half-shell 11 comprises an insertion channel 17 of bone cement, which is, for example, located centrally at the convexity 14, extending from the opposite side, that is, of the cap 130.

The channel 17 constitutes an opening of the convexity 14 which places the forming space in fluid-dynamic communication with the external environment, once the shell 11, 12 has been closed. Preferably, the mould 1 also includes an annular connector 18 which couples with the insertion channel 17 for fluid dynamically connecting the dispenser of the cement in the liquid state (not illustrated) with the interior of the shell 11, 12, that is, with the above-mentioned gap.

In addition, the flange 15 of the female half-shell 11 comprises an inner collar 19, adjacent to the concavity 13, which has one or more channels 190, or tubes, for discharging air from the closed shell 11, 12 after the bone cement has been inserted. The air discharge channels 190 are in communication with the hollow space in the perimetric portion thereof which surrounds the inner space where the spacer is formed.

It should be noted that at its lower side, opposite to that where the convexity 14 protrudes, the flange 16 of the male half-shell 12 can have feet 160 for support on a table or other support.

Furthermore, the invention includes locking means 2 for joining the two half-shells 11, 12 to one another in a removable fashion, that is to say, so as to keep the shell 11, 12 temporarily closed while the spacer is formed and for the cement that it is made of to solidify.

According to the preferred embodiment, shown in FIG. 3, such locking means 2 comprise keys having an engagement shank 21 configured to be inserted in snap-on fashion into through slots 31, 32 formed in the flanges 15, 16 of both of the half-shells 11, 12, which are positioned in such a way that the slots 31, 32 of one are aligned with those of the other, thereby allowing the insertion of the shanks 21 of the keys.

These shanks 21 can include an internal cut 210 forming two foldable tines at the respective free end of which are located locking teeth 211 which protrude transversally, in the opposite direction to the cut 210. Such teeth 211 engage in inner seats defined in shaped cylinders 320 located on the lower surface of the flange 16 of the male half-shell 12, on the side opposite to which the convexity 14 emerges.

A radial abutting flange 22, which can be disc-shaped, is joined on opposite sides to the handgrip 23 and to the inner end of the shank 21 of the key; a thinned section 24 is formed between the flange 22 and the shank 21, which will be broken by the surgeon in order to open the shell 11, 12.

This is only one of the possible embodiments of the locking means 2 of the shell 11, 12. More generally, the locking means 2 can comprise a plurality of locking elements, each suitable to fit into a respective pair of passages 31, 32 of the flanges 15, 16 aligned with one another, to prevent separation of the two half-shells 11, 12 during the forming of the spacer. Each locking element comprises a first portion, which can be inserted in a snap-on fashion in the pairs of aligned passages 31, 32, the end of which first portion forms transversal extensions which abut an outer surface of one of the flanges 16 and a second enlarged portion arranged in correspondence with an outer surface of the other flange 15, opposite the first. In addition, each locking element 211 comprises a thinned section 24 which can be selectively broken, interposed between the first and the second portion.

According to a preferred aspect of the invention, shown in FIG. 2, the inner surface of the concavity 13 of the female half-shell 11 has a variable three-dimensional shape, that is to say, not constant and not smooth.

This allows the creation of cotyle spacers, the convex surface of which, designed to be placed in contact with that of the hip, is texturised, that is to say, it has grooves and/or ribs, depressions and/or peaks which allow a better adhesion of the spacer to the hip.

In fact, the hip bone, when subject to an infection, becomes softer than when it is healthy and this can be exploited, together with the texturised surface of the temporary prosthetic cotyle, in order to obtain better adhesion; it should also be noted that, since the medical cement used for forming the spacer can include antibiotics to combat the infection, better adhesion and co-penetration of the spacer into the surface of the infected area of the hip favours a more efficient release of the drug and can therefore accelerate the treatment.

The texturising of the convex outer surface of the cotyle can be achieved by providing the inner surface of the convexity 14 of the female half-shell 11 with grooves or ribs which may or may not define geometrical patterns or a plurality of repeated protrusions and/or gullies.

The mould of the invention may advantageously be provided with half-shells 11, 12 having concavities 13 and/or convexities 14 with variable dimensions, to allow the definition of internal forming spaces of different dimensions in turn, so as to form spacers of different sizes in order for them to be able to adapt them to the size of the patients.

In practice, the invention also provides a modular mould 11, 12, having the features defined above, essential or optional, obtained from different combinations of half-shells 11, 12.

For example, it can be provided with a modular mould 11, 12 which includes a single male half-shell 12 and three female half-shells 11, having concavities 13 of different dimensions.

The operation of the invention is described below.

The surgeon selects the half-shells 11, 12 suitable for the size of the patient and takes the mould 1 into the operating room.

Firstly, the shell 11, 12 must be closed, with the convexity 14 inserted in the concavity 13, the two flanges 15, 16 in abutment and the keys 2 (or other locking means) inserted in the pairs of aligned slots 31, 32, described above.

Then, the liquid medical cement containing the antibiotic is poured through the insertion channel 17 and fills the forming space, while the air that previously occupied the space exits from the appropriate tubes 190.

Once a sufficient time has passed for the hardening of the cement, the surgeon breaks the keys 2, opens the shell 11, 12 and then extracts the spacer.

At this point, after the fixed prosthesis of the acetabulum has been removed and the infected zone has been treated, the acetabular shape spacer just formed is implanted in the patient, at the hip and the head of the fixed prosthesis of the femur being housed in the concave side of the spacer.

In this way, the patient has been saved the inconveniences he/she is forced to suffer when using the prior art.

The invention claimed is:

1. A mould (1) for forming medical bone cement spacers, the mould (1) comprising:
    a female half-shell (11), provided with a hemispheroidal concavity (13) and
    a male half-shell (12), provided with a hemispheroidal convexity (14) which can be inserted in the concavity (13), to define together with the concavity an internal space for forming the spacer, the internal space having an acetabular shape,
    wherein both the half-shells (11, 12) comprise respective perimetric flanges (15, 16) which centrally form the concavity (13) and the convexity (14),
    wherein the flange (15) of the female half-shell (11) comprises an inner collar (19) adjacent to the concavity (13),
    wherein one or more channels (190) extend from the inner collar (19) in a direction of convexity opposite the male half-shell (12).

2. The mould (1) according to claim 1, the flange (16) of the male half-shell (12) being designed to be shaped to abut the flange of the female half-shell (11), when the convexity (14) of the male half-shell has been inserted in the concavity (13) of the female half-shell, thereby defining the internal space.

3. The mould (1) according to claim 2, comprising locking means (2) for joining the two half-shells (11, 12) to each other in a removable fashion.

4. The mould (1) according to claim 3, wherein on the flanges (15, 16) of both the half-shells (11, 12) there are passages (31, 32), positioned in such a way that the passages of one flange are aligned with those of the other, once one has moved into abutment with the other, the locking means comprising a plurality of locking elements, each designed to be inserted into a respective pair of aligned passages (31, 32).

5. The mould (1) according to claim 4, wherein each locking element comprises a first portion (21), which can be inserted in a snap-on fashion in the pairs of aligned passages (31, 32), the end of which has transversal extensions (211) which abut an outer surface of one of the flanges (16) and a second enlarged portion (22) positioned at an outer surface of the other flange (15), opposite the first, each locking element comprising a thinned broken section (24), interposed between the first and second portions.

6. The mould (1) according to claim 1, wherein said female half-shell (11) comprises a channel (17) designed for fluid-dynamic communication with said internal space and designed for inserting bone cement in the mould (1).

7. The mould (1) according to claim 1, wherein the one or more channels (190) are configured to discharge air following insertion of the bone cement.

8. The mould (1) according to claim 1, wherein an inner surface of the concavity (13) of the female half-shell (11) has a non-constant three-dimensional shape.

9. The mould (1) according to claim 8, wherein the inner surface has grooves.

10. The mould (1) according to claim 8, wherein the inner surface of the concavity (13) has ribs.

11. The modular mould (1) according to claim 1, comprising a plurality of male and/or female half-shells (11, 12) having respective concavities (13) and/or convexities (14) of different dimensions, which can be combined in such a way as to obtain internal forming spaces having different dimensions, so as to allow the formation of spacers of different sizes.

12. The mould (1) according to claim 11, wherein at least one male half-shell (12) of the plurality of male half-shells (12) and two or more female half-shells (11) are provided.

* * * * *